United States Patent
Degim et al.

(10) Patent No.: US 8,057,680 B2
(45) Date of Patent: Nov. 15, 2011

(54) CARTRIDGE FOR ELECTROHEMODIALYSIS

(75) Inventors: Tuncer Degim, Ankara (TR); Rusen Dundaroz, Ankara (TR); Metin Denli, Ankara (TR); Sibel Ilbasmis, Ankara (TR); Tanju Ozcelikay, Ankara (TR); Zelihagul Degim, Ankara (TR)

(73) Assignee: Dizayn Teknik Plastik Boru Ve Elemanlari Sanayi Ve Ticaret A.S., Istanbul (TR)

( * ) Notice: Subject to any disclaimer, the term of this patent is extended or adjusted under 35 U.S.C. 154(b) by 697 days.

(21) Appl. No.: 10/496,053

(22) PCT Filed: Nov. 19, 2002

(86) PCT No.: PCT/TR02/00073
§ 371 (c)(1),
(2), (4) Date: Oct. 29, 2004

(87) PCT Pub. No.: WO03/043681
PCT Pub. Date: May 30, 2003

(65) Prior Publication Data
US 2005/0034991 A1   Feb. 17, 2005

(30) Foreign Application Priority Data
Nov. 19, 2001 (TR) .............. A 2001 03317

(51) Int. Cl.
*B01D 61/42* (2006.01)
*B01D 57/02* (2006.01)
*G01L 1/20* (2006.01)
*C02F 1/469* (2006.01)
*A61M 1/16* (2006.01)

(52) U.S. Cl. ........ 210/646; 204/450; 204/518; 204/527; 204/535; 204/540; 204/550; 204/600; 204/627; 204/629; 204/630; 204/633; 210/645; 210/748.01; 210/252; 210/257.2; 210/243; 210/321.6; 210/321.72; 210/321.75; 210/321.78; 210/321.84

(58) Field of Classification Search .......... 210/645, 210/646, 650, 748, 252, 257.2, 222, 243, 210/321.6, 321.72, 321.75, 321.78, 32.84, 210/321.87, 321.84; 204/450, 516, 517, 204/518, 535, 550, 600, 627, 629, 630, 633, 204/527, 540
See application file for complete search history.

(56) References Cited

U.S. PATENT DOCUMENTS
2,251,083 A * 7/1941 Theorell .............. 204/518
(Continued)

FOREIGN PATENT DOCUMENTS
FR   2.043.917   * 2/1971
(Continued)

*Primary Examiner* — John Kim
(74) *Attorney, Agent, or Firm* — Epstein Drangel LLP; Robert L. Epstein

(57) ABSTRACT

The scope of the invention is to apply an electric current or to use a kind of iontophoresis system with the hemodialysis cartridge and system (the proposed method is also applicable to peritoneal dialysis or other similar methods) to remove unwanted molecules from blood, plasma or serum or other body fluids and to increase the effectiveness of the process. This cartridge can be used for patients with uremia and cartridge fixed to the conventional hemodialysis machine and additionally the electric current applied to the electrodes placed in to the cartridge or electrode connectors placed to the conventional cartridge. When the system activated, the molecules in the blood or other body fluid migrates to the hemodialysis solution. Charged ions or uncharged molecules move together with electroosmotic flow. The sterilized electrodes preferably made by Ag/AgCl to prevent pH changing effect. Other apparatus can also be used for providing an electropotential gradient.

6 Claims, 3 Drawing Sheets

U.S. PATENT DOCUMENTS

| | | | | |
|---|---|---|---|---|
| 2,636,851 A | * | 4/1953 | McRae et al. | 205/517 |
| 3,582,488 A | * | 6/1971 | Zeineh | 204/544 |
| 4,043,895 A | * | 8/1977 | Gritzner | 204/600 |
| 4,351,710 A | * | 9/1982 | Jain | 204/522 |
| 4,461,693 A | * | 7/1984 | Jain | 204/635 |
| 4,549,947 A | * | 10/1985 | Inoue et al. | 204/535 |
| 4,608,140 A | * | 8/1986 | Goldstein | 435/173.9 |
| 4,655,898 A | * | 4/1987 | Poulhes et al. | 204/639 |
| 5,415,628 A | * | 5/1995 | Untereker et al. | 604/20 |
| 5,437,774 A | * | 8/1995 | Laustsen | 204/518 |
| 5,639,368 A | * | 6/1997 | Davis et al. | 210/321.8 |

FOREIGN PATENT DOCUMENTS

| | | | |
|---|---|---|---|
| WO | WO 00/38759 | * | 7/2000 |

* cited by examiner

CARTRIDGE FOR ELECTROHEMODIALYSIS

BACKGROUND OF THE INVENTION

This invention is related to a cartridge and/or a method that provides an additional step of iontophoresis to conventional/classic hemodialysis procedure for those patients who have insufficient kidney functions. It enhances the hemodialysis performance in removing of urea from the blood using electrical potentials. Similarly, it is also related with the procedures such as peritoneal dialysis or related with the procedure when some compounds or molecules (charged or uncharged atoms or molecules, elements or ions) need to be removed from the blood (blood, plasma or serum) to dialysis solution in acute or chronic poisoning cases. It is possible to increase the efficiency of the hemodialysis method and to reduce the total time period of the procedure using this proposed cartridge and/or the method. There are no similar procedures and/or cartridges in use so far.

DESCRIPTION OF THE INVENTION

Basically, hemodialysis is a process to remove urea and some other toxic compounds from blood into the hemodialysis solution by passive diffusion. In this procedure, a semipermeable membrane is used as a dialysis membrane. While the blood is circulating continuously at the one side of the hemodialysis membrane, the hemodialysis solution at the other side, continuously circulates as well. During the process, urea present in the blood at high concentration, depending on the concentration gradient, it passes through the membrane from blood to the hemodialysis solution. Thus, the urea concentration in blood decreases by the time. In conventional hemodialysis procedures, the patient is connected to the hemodialysis machine for about 4 hours, and urea concentration generally decreases to 50% of the beginning level even at the best circumstances.

In iontophoresis procedure, by using an electrical current (creating an electrical potential difference), the ions (molecules or atoms that having a net charge or partially charged) can be carried to the other side of the membrane according to applied current and electrical charge and it is possible to control it. Electrodes or similar tools are provided to the both side of the membrane and the applied electrical current or potential can vary as needed. The ions in the solution/blood migrate according to their charges and their movement is in proportional to the current. For instance positively charged ions migrate to the negative electrode side and vice versa. While the charged ions are migrating according to the electrical current, they also drag the uncharged molecules along with moving molecules. At this instance, traveling from one side to the other side of the membrane creates a flow, a turbulence occurs (this is called an electro-osmotic flow).[1] Therefore the unchanged particles (atoms/molecules) can also be able to pass the membrane by being pulled into this vortex or into the motion and, this passage occurs at a much faster rate than that of passive diffusion.

When the molecular structure of urea investigated, it is seen that some local charges are present on the molecule. According to the experiments we've conducted, the higher urea transportation was observed than passive diffusion and cathodal iontophoresis when urea was present at the positive electrode side because of the positive local charges on the molecule. There is also a possibility that the electroosmotic current was partially influential for this transfer. However, during the transfer, if the other small but charged ions like potassium and sodium are present, the transfer rate decreases; but still the transfer is much larger and faster than the classical method. These experiments were repeated using human blood obtained from the patients with uremia and similar results were achieved. With this invention the hemodialysis procedure is shortened in time and, simultaneously, provided much better result (cleaner blood).

Figure 1:
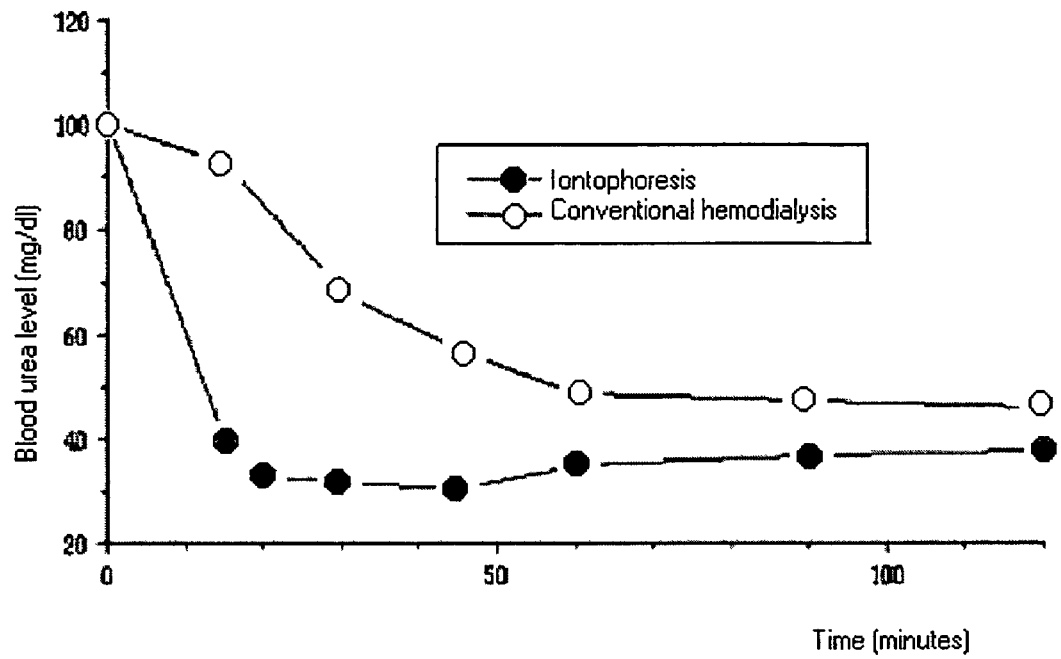
FIG. 1 is a chart showing the urea level change in blood with respect to time, comparatively with the method of the present invention and conventional hemodialysis method.

The previously conducted diffusion experiments were repeated with a peristaltic pump using human blood, hemodialysis solution and the hemodialysis cartridge in new proposed design. In the analysis of the samples taken from the blood that went through the cartridge, it is found that the urea level in blood when the iontophoresis procedure was used prompted 3 to 5 times faster rate of decrease than the classical hemodialysis results. In other words, while the classical hemodialysis procedure takes 4 hours, the iontophoresis procedure of ours lowers the process time to about 30 minutes, and with much better results (FIG. 1).

Figure 2:
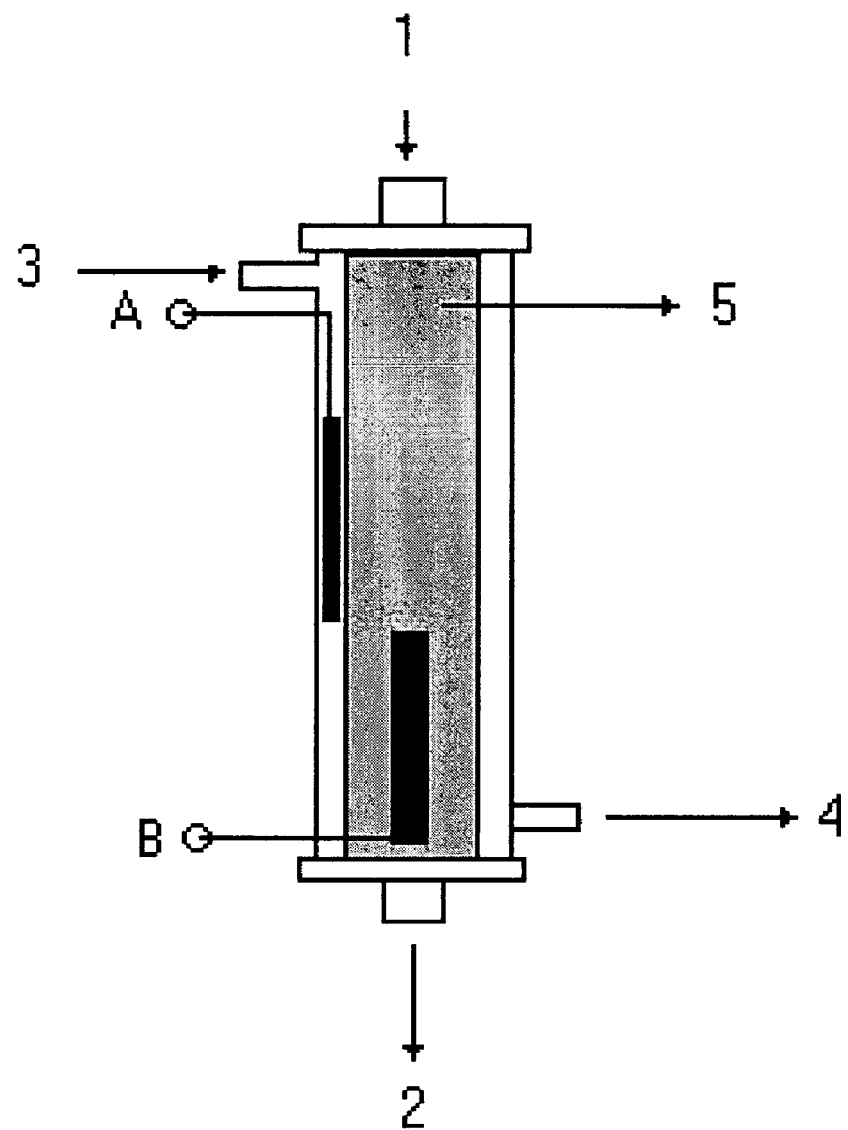
FIG. 2 is a schematic embodiment of the present invention where the electrodes are located respectively inside the blood/plasma compartment and the hemodialysis solution compartment.
Figure 3:
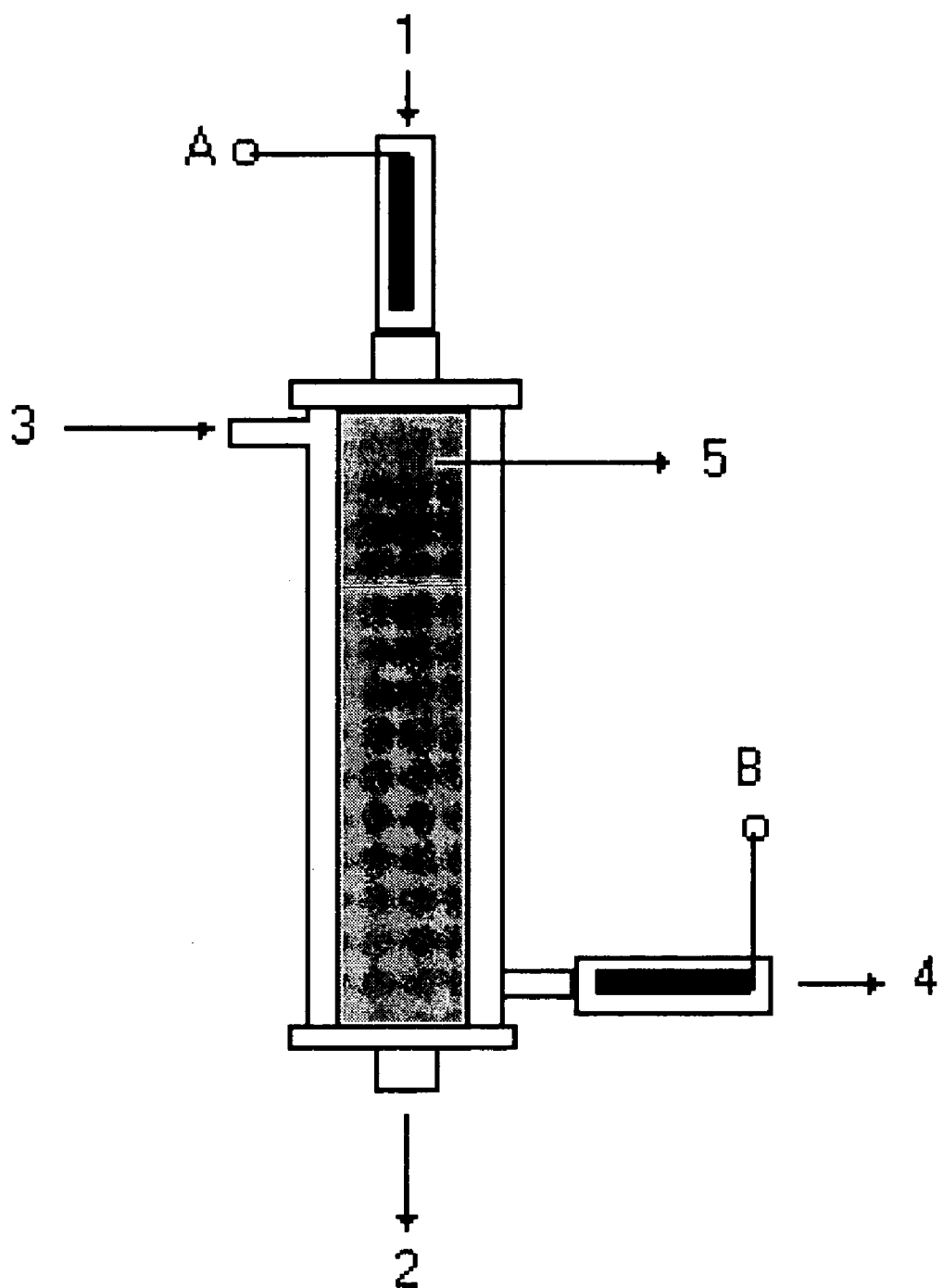
FIG. 3 is a schematic embodiment of the present invention where the electrodes are located respectively at the entry and exit port of the compartments.

If the classical hemodialysis cartridge and proposed iontophoresis procedure is going to be used together; system is depicted in FIG. 2. The cartridge used as a hemodialysis cartridge for removing urea from the blood simply comprises a holding compartment (FIG. -2-1- and FIG. -3-1); and because of the electrodes placed in the cartridge, (FIG. -2-A and B; FIG. -3-A and B) electric current can be applied and that, it is also designed for the use of classical hemodialysis cartridge.

Accordingly, in this figure, the point labeled as 1 indicates the entry of blood and the label 2 shows the exit of the blood. The labels 3 and 4 show the entry and exit points of the hemodialysis solution. The label 5 shows the hemodialysis cartridge's dialysis membrane. The label B shows positive electrode, and label A represents the negative electrode. Thus, when the system is activated, the blood and hemodialysis solution is circulating continuously and electric current is applied and at the end urea can be transferred to the hemodialysis solution with much faster rate. The labels A and B are the electrodes made by Ag and AgCl or they can be designed for same purpose in different shape or compositions. If needed, it is possible to use Ag for B, and AgCl for A. UV or ethylene oxide sterilization can be used for the sterilization of the electrodes.

On the other hand, although the composition of the sterilized electrodes (FIG. -2-A and B; FIG. -3-A and B) is preferred to be Ag/AgCl for preventing the pH effect of the electrodes, they can be also made out of platinum, copper, gold, steel, graphite, vanadium, tungsten, etc. The composition, shape, design, connection point and their place in and outside of the cartridge, are not deterministic and specific properties for the electrodes. Some apparatuses which can be used in formation of electrical gradient may be utilized.

In the experiments, when the electrohemodialysis procedure was used, the sodium and potassium levels of the blood and the hemodialysis solutions have been analyzed. When this procedure used, the level of sodium and potassium is lowered in blood as well. This outcome is possibly same for some other ions and unchanged molecules. For preventing some possible complications, the ions and other material in the hemodialysis solution need to be adjusted. Hemodialysis solutions must be prepared according to the patients' needs. Or, the blood that exited from the hemodialysis cartridge can be connected to another cartridge and similarly ions can be replaced using reverse current and the problem can be solved. The hemodialysis solution(s) (at the beginning and at the supplementary durations) can be prepared according to the needed requirements of the patient to avoid any possible complications.

Additionally, in these complications (the problems like imbalance of electrolytes and/or osmotic pressure or similar unwanted outcomes due to iontophoresis) problems can be overcame by producing a membrane that would have smaller pores. With two membranes present in one, first one allows the unwanted urea and the other molecules does not allowed by second material to go through. The application of electrical current to both membrane or by applying the classical methods to the second one (utilizing only the concentration gradient) the possible problems can be avoided.

There is no research and experiments that have been published so far, the application of electrical current or potential and the gradual electrical effect have not been tried for the hemodialysis or peritoneal dialysis or removing unwanted molecules, ions etc. from the blood or other body fluid using a system like our proposed system here. In this study, the addition of iontophoresis procedure, in terms of shortening the time duration and bettering the quality of outcome, is a revolutionary format that is at the cutting edge of the known medical technology. In the literature there is no study or research have been conducted to this end.

This invention, in addition to its speed and quality in the treatment of uremia, it has a high potential of removing unwanted/unneeded non-polar and especially polar substances during the acute and chronic poisoning; similarly with electrical current and the cartridge usage the unwanted items/substances in the blood can be pulled out into the hemodialysis solution. In the literature we came across that the electrical current lesser than 0.5 mA/cm$^2$ does not cause damage to the blood or body cells[1]. For this reason the current that is low than 0.5 mA/cm$^2$ would be an acceptable for a positive out come. The magnitude of the current can be chosen in required levels. For the system, direct or alternative current, square, sinus or triangular or even different frequencies and/or currencies can be applied. In this system, the electrical flow/current does not make any direct contact with any of the body cells; and therefore, it would be possible to exceed the electrical level of the aforementioned literature. However, because there is a likelihood of damaging the blood cells during a high currency flow this would not be recommended.

Additionally, the pH levels was not affected by the Ag/AgCl electrodes, therefore we preferred. Electrodes can be made with different compounds or also some similar apparatuses with similar functions can be used. The electrodes may even be simply attached to the classical hemodialysis cartridges' blood and hem-dialysis solution's entry ports (FIG. 3). If the available classical hemodialysis cartridge will be used, an alternative placement of the electrodes are shown in FIG. 3. In this model, the electrodes can be attached to blood entry port and hemodialysis solution part as in the previous cases, and the classical hemodialysis cartridge can be used with minimal modifications. (In this model, electrodes in different composition or some apparatus with similar functions can be used). The electrodes themselves need to be sterilized. In FIG. 3, the labels 1,2,3,4 and 5 are the same labels as shown in FIG. 2.

As a result, this invention will prevent those patients who have insufficient kidney functions being hooked up to a hemodialysis machine for a long time. It will provide for the urea, creatine, and some toxic compounds to exit the blood in a better way. Additionally, the procedure's potential of removing the unwanted elements from the patient's blood stream in acute and chronic poisonings will provides a very valuable device in the field of medicine.

With the exception of electrodes and similar apparatuses, the cartridge being proposed, in terms of shape and dimensions is very similar to those cartridges used in classical hemodialysis. The difference of the cartridge, such as surface area or its membrane with different pore sizes, alone is not a distinctive quantification of the proposed device for patent purposes. The sizes, compositions, or locations (such as one being by the blood inflow side and the other being by the dialysis side or the solution) of the electrodes and/or some apparatuses with similar functions do not restrict its applicability for patent rights.

Additionally, the composition of the hemodialysis solution, the properties of the dialysis membrane (color, texture, latex or biological tissue, pore size, selectivity, etc.), the way, the flow intensity and the direction of the blood, hemodialysis solution and the number of cartridge used connected before or after each other are not also deterministic and specific properties of the invention.

REFERENCE

1—M. J. Pikal, "The role of electro-osmotic flow in transdermal iontophoresis," Advanced Drug Delivery Reviews, 46, 281-305,2001.

The invention claimed is:

1. A method for improving passive diffusion of urea and other toxic substances during the hemodialysis through Iontophoresis utilizing a cartridge having first and second compartments separated by a semi-permeable membrane, the method comprising the steps of:
   a. connecting the body of the patient and the first compartment of the cartridge with a first conduit;
   b. connecting a source of hemodialysis solution and the second compartment of the cartridge with a second conduit;
   c. circulating blood/plasma through the first conduit from the patient and through the first compartment;
   d. continuously circulating the hemodialysis solution through the second conduit from the source of hemodialysis solution and through the second compartment;
   e. providing a positive electrode in the continuously circulating blood/plasma;
   f. providing a negative electrode in the continuously circulating hemodialysis solution;
   g. applying a constant electrical current at the electrodes, the current density being less than 0.5 mA/cm$^2$; and
such that the charged urea and other toxic substances in the blood/plasma are transferred through the membrane into the solution by electrical forces and neutral or partially charged substances are also transferred to the solution by means of an electroosmotic flow obtained by the movement of the charged substances, whereby a higher flow rate is achieved compared to the passive diffusion.

2. The method of claim 1 wherein the first and second electrodes comprise Ag and AgCl, respectively.

3. The method of claim 1 wherein the method is used for the treatment of renal failure, acute and chronic poisoning, and peritoneal dialysis.

4. A device for improving passive diffusion of urea and other toxic substances during the hemodialysis through Iontophoresis comprising:

a cartridge having a blood or plasma compartment and a hemodialysis solution compartment separated by a semi-permeable membrane;

a first conduit;

means for connecting the body of the patient and said blood/plasma compartment of said cartridge with said first conduit;

a second conduit;

means for connecting a source of hemodialysis solution and the hemodialysis solution compartment of the cartridge with said second conduit;

means for continuously circulating blood/plasma through said first conduit from the patient and through said blood/plasma compartment;

a source of hemodialysis solution;

means for continuously circulating the hemodialysis solution through said second conduit from said source of hemodialysis solution and through said hemodialysis solution compartment;

a positively charged electrode situated in the blood/plasma compartment;

a negatively charged electrode situated in the hemodialysis solution compartment;

means for applying a constant electrical current at electrodes, the current density being less than 0.5 mA/cm$^2$; and such that the charged urea and other toxic substances in the blood/plasma are transferred through the membrane into the solution by electrical forces and neutral or partially charged substances are also transferred to the solution by means of an electroosmotic flow obtained by the movement of the charged substances, whereby a higher flow rate is achieved compared to the passive diffusion.

5. The device of claim 4 wherein said first and second electrodes comprise Ag and AgCl, respectively.

6. The device of claim 4 for use for the treatment of renal failure, acute and chronic poisoning, and peritoneal dialysis.

* * * * *